(12) United States Patent
Heckmeier

(10) Patent No.: US 6,317,201 B1
(45) Date of Patent: Nov. 13, 2001

(54) METHOD FOR THE DETERMINATION OF REFRACTIVE INDICES AND OPTICAL INSTRUMENT THEREFOR

(75) Inventor: Michael Heckmeier, Bensheim (DE)

(73) Assignee: Merck Patent Gesellesschaft, Darmstadt (DE)

(*) Notice: Subject to any disclaimer, the term of this patent is extended or adjusted under 35 U.S.C. 154(b) by 0 days.

(21) Appl. No.: 09/399,148

(22) Filed: Sep. 20, 1999

(30) Foreign Application Priority Data

Sep. 19, 1998 (EP) .................................................. 98117825

(51) Int. Cl.$^7$ ..................................................... G01N 21/41
(52) U.S. Cl. ......................... 356/128; 356/135; 356/136
(58) Field of Search ................................... 356/128, 135, 356/136, 137

(56) References Cited

U.S. PATENT DOCUMENTS 5,565,978 * 10/1996 Okubo et al. ........................ 356/128

OTHER PUBLICATIONS

Optical Anisotrophy by U. Finkenzeller et al., part IV of "Physical Properties of Liquid Crystals," Nov. 1997, pp. 1–5.

"Ekisho Kisohen" by K. Okano et al., (Jul. 15, 1985 and Jun. 15, 1989). ISBN–563–03414–2, chapter 10.3.1, pp. 212–213.

Abbe Refraktometer B, manual of operation, Zeiss, Germany, Date Not Available.

* cited by examiner

Primary Examiner—Hoa Q. Pham
Assistant Examiner—Amanda Merlino
(74) Attorney, Agent, or Firm—Millen, White, Zelano & Branigan, P.C.

(57) ABSTRACT

The present invention relates to a method for the determination of refractive indices, ranging over a wide range of values. It also relates to a method for the determination of the birefringence of liquid crystals. Further, it relates to optical instruments used for such determinations.

22 Claims, 1 Drawing Sheet

METHOD FOR THE DETERMINATION OF REFRACTIVE INDICES AND OPTICAL INSTRUMENT THEREFOR

FIELD OF THE INVENTION

The present invention relates to a method for the determination of the refractive index of a liquid material, a material dispersed in a liquid material or a liquid crystal material and to the optical instrument used for this determination. It further is especially related to the determination of the birefringence of liquid crystals.

BACKGROUND OF THE INVENTION

Liquid crystal materials are of high commercial interest due to their beneficial use in electro-optical displays.

The electro-optical displays use electro-optical effects exploiting the electrical, respectively dielectrical, and the optical anisotropy properties of the liquid crystal materials. Thus, for application of liquid crystals to such effects, it is essential to assess besides the dielectrical properties of the liquid crystal materials, i.e. the dielectric permittivity parallel to the director ($\epsilon_{||}$), the dielectric permittivity perpendicular to the director ($\epsilon_\perp$) and their difference, the dielectric anisotropy ($\Delta\epsilon=\epsilon_{||}-\epsilon_\perp$), also their optical properties, i.e. the refractive index parallel to the director, called the extraordinary refractive index ($n_e$), the refractive index perpendicular to the director, called the ordinary refractive index ($n_o$) and their difference, the anisotropy of the refractive indices, called birefringence in this application ($\Delta n=n_e-n_o$).

Most widely used today are nematic liquid crystals consisting of calamitic, i.e., rod-like molecules which are characterized by an orientation of their long molecular axis which is on average parallel to a preferred direction. This preferred direction is generally referred to as the director.

Thus, in an oriented sample, nematic liquid crystals are characterized by anisotropic physical properties. i.e. their physical properties depend on the orientation relative to the director. Nematic liquid crystals generally are rotational symmetric to the axis of the director. This is called uniaxially anisotropic. Thus most of their physical properties, like e.g. refractive index, dielectric permittivity and magnetic susceptibility, adopt two different values when viewed either parallel or perpendicular to the director.

The expert has several methods available to determine the birefringence of liquid crystal media especially of nematic liquid crystal media.

Among the known methods are the use of the so called Leitz-Jelly refractometer and the use of refractometers exploiting the determination of the critical angle of total reflection, as for example the so called Abbe refractometer.

The refractometer according to Leitz-Jelly consists of a back plane comprising a slit and a measuring scale and of a sample holder. The sample holder features a wedge-shaped space between a flat transparent body and a prism. This prism is located on the opposite side of the back plane. On the side of the flat transparent body of the sample holder which faces the back plane a nontransparent plate with a narrow hole is affixed.

The liquid crystal is oriented between the flat transparent body and the prism. When it is now illuminated from the back, the light passing through the slit in the back plane and through the small hole in the nontransparent body behind the sample holder passes the sample being split into an ordinary and an extraordinary beam.

The observer, located at the prism side of the sample holder can then determine the imaginary origins of both beams on the graded scale of the back plane.

The use of the Leitz-Jelly refractometer is briefly explained e.g. in "Ekisho Kisohen" by K. Okano and S. Kobayashi. Kabushiki Kaisha Baifukan (Jul. 15, 1985 and Jun. 15, 1989). ISBN-563-03414-2, chapter 10.3.1, pp. 212–213.

The use of the Abbe refractometer is e.g. described in "Optical anisotropy" by U. Finkenzeller and R. E. Jubb, part IV of "Physical properties of liquid crystals", status November 1997, Ed. W. Becker, Merck KGaA, Germany.

These methods, especially the latter one, have the advantage that both the ordinary and the extraordinary refractive index and thus also their difference, the birefringence, can be determined almost at the same time for one and the same sample. Thus there is no uncertainty about any change in conditions which would influence the refractive indices, like the orientation of the sample and the temperature of the sample. In fact, by the method using the Abbe refractometer the ordinary and the extraordinary refractive index of the material are determined not simultaneously but subsequently only, but a change in the boundary conditions and in the surroundings can be practically excluded by repetition of the previous readings. Thus this method is a "quasi-simultaneous" measurement method.

The method using a Leitz-Jelly refractometer allows the determination of a wide range of both $n_e$ and $n_o$ values and thus also of $\Delta n$ values, however the accuracy of this method is only about ±0.001 for both $n_e$ and $n_o$ and thus only ±0.002 for $\Delta n$.

Consequently for most practical applications the method using the Abbe refractometer, having, at least ideally, an accuracy of ±0.0002 for the refractive indices $n_e$ and $n_o$ and of ±0.0004 for the birefringence $\Delta n$ is preferred.

Problem to be Solved by the Invention

The Abbe refractometer is one example of refractometers employing the principle of the critical angle of total reflection between two optically transparent media with different refractive indices. Thus, naturally but unfortunately, the range of refractive indices accessible using this refractometer, like others based on the same measuring principle, depends on the refractive index of the measuring body used, which typically is a measuring prism.

The total range of refractive indices accessible by commercially available Abbe refractometers (e.g. by Zeiss, Germany) ranging from 1.17 to 1.85 is already rather wide, but it is only accessible with three different measuring prisms. One prism allowing measurements in the range of 1.17 to 1.56, the next one from 1.30 to 1.71 and the last one from 1.45 to 1.85 (Abbe refractometer B, manual of operation, Zeiss, Germany).

Thus refractive indices of compounds varying over a wide range of values can only be determined using different measuring prisms. On the one hand, exchanging the prisms of a refractometer is rather economical, however it takes an appreciable amount of time, especially considering the time required for thermostating the different prisms. It also increases the risk of damaging the prisms due to more frequent handling and exposure. On the other hand, the parallel use of different refractometers is more time efficient, but less economic.

Further, recently there is an increasing demand for liquid crystal materials with large birefringence values even with $\Delta n>0.4$. In order to determine the birefringence of such materials, as well as e.g. the birefringence of materials with $n_o$ in the range from 1.3 to 1.45 and $\Delta n$ in the range from 0.25 to 0.40, it is necessary to conduct two separate measurements of $n_e$ and $n_o$ either changing the measuring prisms of the refractometer between measurements or using two refractometers with different prisms. Both these methods, however, lead to the loss of the benefits of the simultaneous or almost simultaneous measurement.

Thus, uncertainties due to possible differences in measurement conditions, especially such as orientation of the sample and measurement temperature, lead to a smaller accuracy and even to systematic errors.

Thus it is highly desirable to maintain the benefits of the measuring method using e.g. the Abbe refractometer, i.e., the good measurement accuracy and the at least quasi simultaneous measurement and at the same time to significantly enlarge the accessible range of refractive indices.

SUMMARY OF THE INVENTION

It has now been found that the problem of the limited range of refractive indices which are accessible quasi simultaneously with a refractometer measuring the critical angle of reflection, e.g., an Abbe refractometer, can be solved by using a measuring body, e.g., a measuring prism comprising at least two parts of transparent material with different refractive indices.

DETAILED DESCRIPTION OF INVENTION

One embodiment of the optical instrument of the instant invention is an Abbe refractometer comprising a measuring prism comprising at least two partial prisms of transparent material with different refractive indices.

Preferably the refractometer comprises a measuring body which is constructed of two or more parts of solid, optically transparent materials at least two of which have different refractive indices from each other.

The measuring body may have different shapes. Possible shapes are e.g. rhomboedrical bodies, triclinic bodies, cuts of tri- or polygonal columns or other shapes. Cuts of columns are preferred. These cuts may have varying cut surfaces, plane cut surfaces are preferred. In particular plane cut surfaces which are parallel or inclined to each other are preferred. When the cut surfaces are parallel to each other they can be inclined or parallel to the other edges of the tri- or polygonal columns. Amongst measuring bodies which are cuts of tri- or polygonal columns with parallel cut surfaces such cuts with cut surfaces orthogonal to the edges of the polygonal columns are particularly preferred. These bodies are commonly called prisms. Another preferred embodiment of the measuring body according to the instant invention is a cut of a tri- or polygonal column with cut surfaces inclined to each other. These wedge-shaped cut surfaces can be, e.g., exploited to fix the at least two parts of the measuring body (i.e., measuring wedge shaped prism) by a suitable fixing means, e.g., a wedge-shaped housing. Most preferred are measuring bodies with inclined cut surfaces or with parallel surfaces orthogonal to the other edges. The latter ones, also called prisms, are particularly preferred.

Said at least two materials of the measuring body which have different refractive index are preferably optically isotropic.

Examples of such optically isotropic or almost isotropic materials are various glasses and crystals.

Typical glasses with different refractive indices are known with refractive indices ranging from, e.g., $n_d=1.458$ ($n_d$ refers to the refractive index at the He-line of 587.6 nm) and $n_D=1.458.4$ for 96% $SiO_2$ silicate glass or quartz glass ($n_D$ refers to the refractive index at 589.3 nm, the sodium D line doublet over $n_D=1.545$ soda-lime-lead glass to $n_D=1.693$ for lead glass with a high lead content.

Crystalline transparent solid media are, e.g., Quartz with $n_{D,o}=1.5442$ and $n_{D,e}=1.5533$, $ZrO_2$ with $n_D=2.13$ (D'Ans Lax), $TiO_2$ (Rutile) $n_{D,o}=2.6158$, $n_{D,e}=2.9029$, $TiO_2$ (Anatase) $n_{D,o}=2.534$, $n_{D,e}=2.493$, and $TiO_2$ (Brookite) $n_{D,1}=2.5832$, $n_{D,2}=2.5856$, $n_{D,3}=2.7414$. The $n_D$ values representing the refractive indices (sodium doublet line at 589 nm); the o and e directed to ordinary and extraordinary properties; and for $TiO_2$ (Brookite), the numbers 1–3 directed to three refractive indices for this material.

Anisotropic, transparent, solid materials are preferably transformed into their glass-states, e.g., by heating into the liquid state and subsequent rapid cooling, prior to their use as materials for the measuring body according to the instant invention. However, also other macroscopically isotropic states of these materials, like, e.g., amorphous states with randomly oriented microcrystallines, can be beneficially used.

The difference of the refractive indices of at least two of the at least two parts of the measuring body are different at least by 0.05 preferably by at least 0.1 and most preferably by at least 0.3. The differences are, however, preferably not more than 1.2, most preferably not more than 0.9.

It is, however, also possible to combine two or more parts to one body, each part consisting of different materials described herein, e.g., for the measuring prisms commercially available. The three measuring prisms available from Zeiss, Germany successively cover the ranges of refractive indices:

| No. | range     | type                |
|-----|-----------|---------------------|
| 1   | 1.17–1.56 | for low $n_D$       |
| 2   | 1.30–1.71 | standard            |
| 3   | 1.45–1.85 | for high $n_D$      | according to the brochure "Abbe Refractometer B, Gebrauchsanleitung" (manual of operation).

Thus, the combination of the materials of the two measuring prisms Nos. 1 and 3 according to the instant invention covers the range of refractive indices over the combined range from 1.17–1.85.

The at least two parts of the measuring body are shaped in such a way that both have a surface, which preferably is a plane surface, to hold the material whose refractive index respectively indices are to be determined.

These surfaces are preferably parallel and preferably adjacent to each other, mos preferably they are adjacent to each other in the same plane.

Further, all of the at least two parts of the measuring body have at least one, preferably plane surface, for the exit of the measuring light. These surfaces preferably are parallel to each other and most preferably are in the same plane.

Thus preferably a combined measuring body is realized which comprises of least two, i.e. two or more, parts with different refractive index.

The geometry of this combined measuring body is by no means restricted to a certain shape and those skilled in the art can easily find and define various suitable shapes.

In a preferred embodiment, the combined measuring body is a prism which preferably is constructed in such a way, as to replace commercially available measuring prisms, i.e. it has the same shape and (dimensions) volume as the commercially available measuring prisms, e.g. those available from Zeiss, Germany.

As generally the measuring prisms used in Abbe refractometers are passed by the measuring light transversally, in a preferred embodiment of the present invention the inventive prism comprises at least two parts which are sub-prisms characterized in that they are identical in all angles and in all dimensions except one. This one dimension is the thickness of the prism, i.e. its extension in the surface which is in contact to the substance to be investigated and perpendicular to the path of the light beam. This dimension is also known as the height (h) of the prism. Please refer also to FIG. 1.

Obviously, in the same manner more than two parts i.e. three or more parts, preferably sub-prisms, can be combined to build a measuring body preferably a measuring prism. Then two of the parts preferably sandwich one or more parts. All of these parts can have different refractive indices, e.g. if the body comprises three parts i=1 to 3, the refractive index $n_i$ of each one of these can have a different one of the refractive indices of the three materials of the prisms Nos. 1 to 3 available from Zeiss, Germany mentioned above. However, it is also possible that two or more of the parts have identical refractive indices, as long as at least one of the parts has a refractive index which is different from that of the others. Thus it is, e.g. possible that two parts, preferably sub-prisms, with identical refractive index, sandwich a third part, again preferable a sub-prism, with a different refractive index. It is also possible that for example four parts in two pairs of mutually identical refractive index are used. In this or similar cases the parts with different refractive indices preferably are alternating in the measuring body.

Preferably the measuring body according to the instant invention comprises two to four parts at least two of which have different refractive indices. Especially preferably the measuring prism comprises two or three, particularly two, parts of which at least two have different refractive indices.

The heights $h_i$ of the respective parts i may be identical to each other or different from each other.

Preferably the materials of the different parts of the measuring body are selected in such away that their coefficients of thermal expansion are compatible with each other in order to avoid or minimize thermal stress. In case an adhesive is used to fit the different parts of the measurement body together the adhesive is also selected to have a similar coefficient of thermal expansion compared to those of the respective parts combined by the adhesive. Preferably the adhesive has a thermal expansion coefficient which lies in between the values of the bodies joined by the adhesive, especially if these are rather different so as to minimize thermal stress. It is, however, also possible to use an adhesive with plasticity to reduce thermal stress.

The combination of the at least two parts of the measurement body can be realized by various ways known in the art. In a simple way they can be adhesion fitted. In this case, however, optionally a frame can be applied to prevent unintentional moving of the parts relative to each other. Using adhesion fitting, further great care has to be taken to assure excellent flatness of the surfaces of the parts contacting each other to fit the parts by adhesion, not only to have optimum adhesion forces but also in order to avoid contamination of the gap between the parts by the substance to be investigated. Adhesion fitting may be supported or even replaced by fitting via suitable recesses and respective cutouts in the respective parts of the measuring body.

Another suitable way to combine the parts of the measuring prism is to glue them together. Conventional glue can be applied. However, the glues used have to be selected such that they are compatible with, i.e. insoluble, in the materials to be investigated, thermally stable (preferably at least up to 100° C.) and have suitable optical properties to not interfere with the measuring light beam too much. Depending on the refractive indices of the adjacent parts of the measuring prism different glues may be used even in one prism. Under certain conditions, anisotropic materials, like liquid crystalline polymers can be beneficially used as glues. The precursors of these can be oriented on the surfaces prior to curing.

If a measuring body is used, which according to one preferred embodiment of the instant invention has a prism shape with the cut surfaces of the column being inclined to each other, called wedge shaped prism here, fitting may be enhanced or even completely achieved by applying a fixing means, e.g. a pressure frame of suitable shape, e.g. wedge shape.

Preferably the liquid crystal samples investigated with the optical instrument according to the instant invention using the method of the instant invention are uniformly aligned on the measuring body and especially preferably they are uniformly aligned and sandwiched between the measuring body and the illumination body. Preferably the alignment is homeotropic. In a preferred embodiment at least one of the bodies is, preferably both are, covered with an aligning agent such as, for example, lecithin. The application can be achieved by rubbing with a cloth wetted with a solution of lecithin in a suitable solvent preferably trichloroethane.

Determination of the ordinary refractive index is possible by application of polarized light or simply by placing a polarizer, acting as an analyzer, on the eyepiece of the measuring instrument, as described e.g. by Finkenzeller and Jubb. The extraordinary refractive index can be determined independent of the use of a polarizer.

All references and documents cited in this application and the foreign priority document EP 98 117 825.4 are incorporated by reference. This holds, amongst others, especially for "Optical anisotropy" by U. Finkenzeller and R. E. Jubb, part IV of "Physical properties of liquid crystals", status November 1997, Ed. W. Becker, and "Abbe Refractometer B, Gebrauchsanleitung (manual of operation) Zeiss, Germany.

Figure 1:
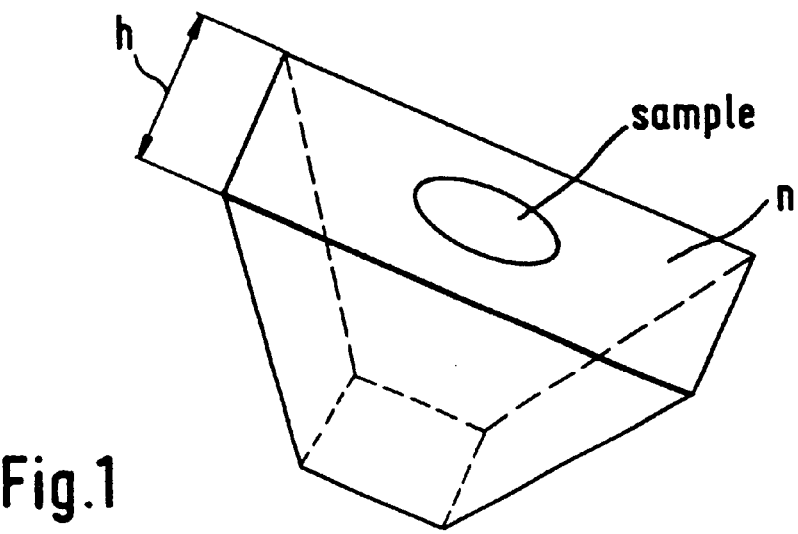
FIG. 1 shows a schematic drawing of a measuring prism, giving the height of the prism h.
Figure 2:
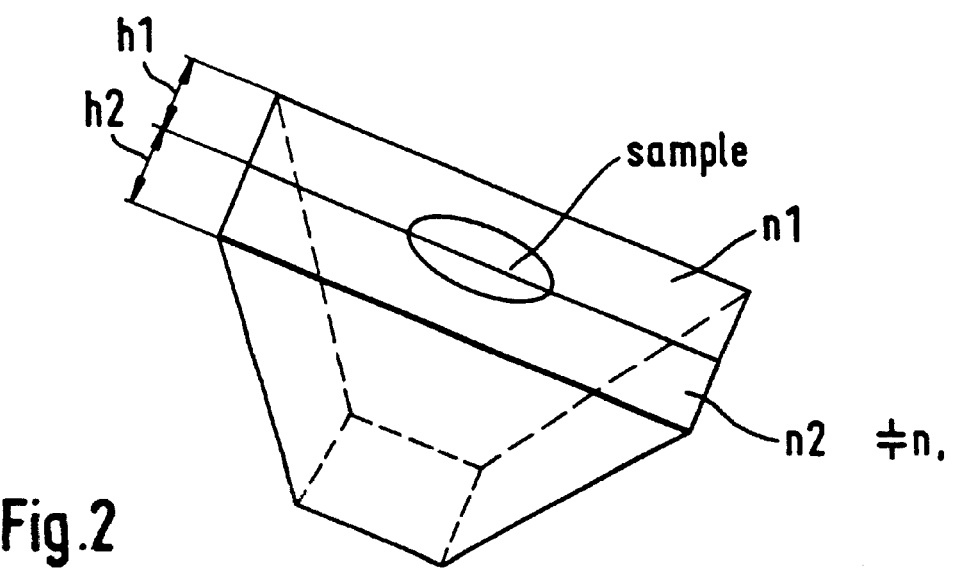
FIG. 2 shows an example of a preferred embodiment of a prism according to the instant invention. $n_1$ and $n_2$ are the respective refractive indices of the two optically transparent media. $h_1$ and $h_2$ are the respective heights of the two sub-prisms comprised in the prism.

In this application, unless explicitly stated otherwise at each occurrence, all temperatures are given in degrees centigrade, i.e., Celsius (°C.), all temperatures are given in difference of degrees centigrade (degrees), all physical data are specified at and for 20° C., all refractive indices are given for the wavelength at the sodium doublet line at 589.3 nm, generally indicated by the index "D" in $n_D$ and all concentrations are given in mass percent.

EXAMPLES

The following examples shall illustrate the present invention without limiting it in any way. Compounds of liquid crystal materials are given in this application by abbreviations which are listed in the following table.

TABLE 1

Abbreviations of liquid crystal compounds

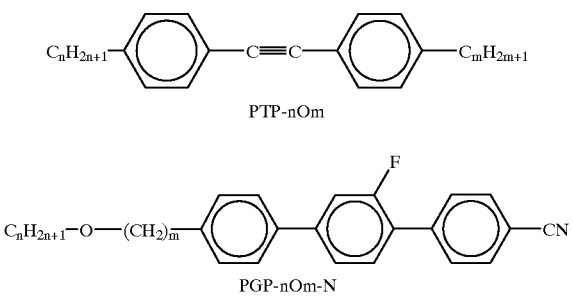

PTP-nOm

PGP-nOm-N

These compounds are standard products of Merck KGaA, Darmstadt or accessible by known methods.

Example 1

A measuring prism is prepared comprising two parts, each being a sub-prism of the shape and size of the prisms Nos. 1 and 3 available from Zeiss, Germany, mentioned in the text above, with the one exception that each sub-prism has only one half of the height of the commercially available prisms. The two parts are combined by adhesion fitting and inserted into the space for the measuring prism of a commercially available "Abbe refractometer B" of Zeiss Germany. The measuring prism was covered with a film of lecithin by repeated unidirectional buffing with a cloth wetted with a 0.1% solution of lecithin, Merck KGaA (Art. No. 5331) in trichloroethane (also from Merck KGaA). The cloth being wrapped around a cylindrical rod of teflon® with a diameter of about one centimeter and a length of about 20 centimeters.

The illumination prism was on its planar side, which later contacted the measurement sample, also covered with lecithin in the same manner as the measuring prism.

The measuring prism was covered with a small drop of approximately 50 µl of the liquid crystal mixture A, the composition of which is given below, and subsequently covered with the illumination prism. After closing of the refractometer the sample was thermostated at 20° C. for 30 minutes. Then first the ordinary refractive index was determined as 1.4417

Subsequently the extraordinary refractive index was determined as 1.7738 and again the ordinary index was determined and confirmed to be 1.4417, within experimental accuracy.

TABLE 2

| | Mixture A Composition | |
|---|---|---|
| Compound No. | Compound Abbreviation | Concentration/ Weight-% |
| 1 | PGP-103-N | 92.0 |
| 2 | PTP-102 | 4.0 |
| 3 | PTP-201 | 4.0 |

Physical properties 153° C.
T (N, I)/° C.

Thus for a given sample, i.e. with the same orientation and at the same temperature the birefringence $\Delta n$ has been determined as $\Delta n = n_e - n_o = 1.7738 - 1.4417 = 0.3321$.

Comparative Example 1

The refractive indices of the liquid crystal mixture A have been determined with Abbe refractometers with conventional measuring prisms.

The ordinary refractive index was only accessible with a refractometer with a measuring prism ranging from 1.30 to 1.71 and the extraordinary refractive index only with a refractometer with a prism ranging from 1.45 to 1.85.

The sample preparation and conditioning was performed as described in example 1. The ordinary index of refraction as well as the extraordinary refractive index were determined with values identical within experimental error to those obtained in Example 1.

What is claimed is:

1. A method for determining the refractive index of a material using a refractometer measuring the critical angle of reflection, wherein the refractometer comprises a measuring body comprising at least two parts of optically transparent material with refractive indices which are different from each other, wherein the measuring body is a measuring prism.

2. The method according to claim 1, wherein the light beam of the refractometer passes as least one part of each of said at least two parts of the measuring body.

3. The method according to claim 1, wherein the at least two parts of the measuring prism are prisms, i, with the same shape and size except that their respective heights, $h_i$, may be identical or different from each other.

4. The method according to claim 1, wherein the material which is subject to the determination of its refractive index is a liquid crystal material.

5. The method according to claim 2, wherein the material which is subject to the determination of its refractive index is a liquid crystal material.

6. The method according to claim 3, wherein the material which is subject to the determination of its refractive index is a liquid crystal material.

7. The method according to claim 4, wherein the liquid crystal material is aligned on the measuring body.

8. An optical instrument for the determination of the refractive index of: a liquid, a solid dispersed or immersed in a liquid or a liquid crystalline media, which instrument is capable of determining the critical angle of total reflection and comprises a measuring body having two or more parts with refractive indices which are different from each other, wherein the measuring body is a measuring prism.

9. The optical instrument of claim 8, wherein said two or more parts are prisms of the same shape and size with the exception that their respective heights may be identical or different.

10. The method of claim 4, wherein the liquid crystal material is an oriented liquid crystal.

11. The method of claim 1, wherein the at least two parts of optically transparent material have refractive indices differing by at least 0.05.

12. The method of claim 1, wherein the at least two parts of optically transparent material have refractive indices differing by from 0.1 to 1.2.

13. The method of claim 1, wherein the at least two parts of optically transparent material have refractive indices differing by from 0.3 to 0.9.

14. The instrument of claim 8, wherein the two or more parts have adjacent plane surfaces on the same plane.

15. The method of claim 1, wherein the measuring body has three measuring prism parts: one covering refractive indices of 1.17–1.56, one covering refractive indices of 1.30–1.71, and one covering refractive indices of 1.45–1.85.

16. The method of claim 1, wherein the measuring body has two measuring prism parts: one covering refractive indices of 1.17–1.56 and one covering refractive indices of 1.30–1.71.

17. The method of claim 1, wherein the measuring body has two measuring prism parts: one covering refractive indices of 1.30–1.71 and one covering refractive indices of 1.45–1.85.

18. The method of claim 1, wherein the measuring body has two measuring prism parts: one covering refractive indices of 1.17–1.56 and one covering refractive indices of 1.45–1.85.

19. The instrument of claim 8, Wherein the measuring body has three measuring prism parts: one covering refractive indices of 1.17–1.56, one covering refractive indices of 1.30–1.71, and one covering refractive indices of 1.45–1.85.

20. The instrument of claim 8, wherein the measuring body has two measuring prism parts: one covering refractive indices of 1.17–1.56, and one covering refractive indices of 1.30–1.71.

21. The instrument of claim 8, wherein the measuring body has two measuring prism parts: one covering refractive indices of 1.30–1.71 and one covering refractive indices of 1.45–1.85.

22. The instrument of claim 8, wherein the measuring body has two measuring prism parts: one covering refractive indices of 1.17–1.56 and one covering refractive indices of 1.45–1.85.

* * * * *